United States Patent
Porper et al.

[11] Patent Number: 6,138,310
[45] Date of Patent: Oct. 31, 2000

[54] ELECTRIC TOOTHBRUSH HAVING OPPOSED BRISTLE HEADS

[76] Inventors: Robert P. Porper, Mill Pong Offices, Suite #200, 293 Rte. 100, Somers, N.Y. 10589; Robert G. Dickie, 15 Valley Trail, Newmarket, Canada, L3Y 4V8

[21] Appl. No.: 09/296,631

[22] Filed: Apr. 23, 1999

[51] Int. Cl.⁷ .................................................. A46B 13/02
[52] U.S. Cl. ............................................ 15/22.2; 15/22.1
[58] Field of Search .................................. 15/22.1, 22.2, 15/167.2

[56] References Cited

U.S. PATENT DOCUMENTS

| | | |
|---|---|---|
| D. 259,977 | 7/1981 | Porper . |
| 5,027,463 | 7/1991 | Daub . |
| 5,259,083 | 11/1993 | Stansbury, Jr. . |
| 5,327,607 | 7/1994 | Wagner . |
| 5,353,460 | 10/1994 | Bauman . |
| 5,359,747 | 11/1994 | Amakasu . |

FOREIGN PATENT DOCUMENTS 4215705  8/1992  Japan ................................... 15/167.2

*Primary Examiner*—Randall E. Chin
*Attorney, Agent, or Firm*—Marks & Clerk

[57] ABSTRACT

An electric toothbrush is provided with an electric motor and a driving mechanism. The driving mechanism includes a drive shaft having a longitudinal axis, and is adapted for frictional coupling to a drive pin mounted on a brush head portion of the electric toothbrush so as to impart a linear reciprocating motion in a direction along its longitudinal axis. The brush head portion comprises a pair of opposed bristle head portions arranged so as to present two groups of opposed bundles of bristles disposed substantially perpendicularly each to the other. Each of the groups of bundles of bristles comprises a plurality of rows and a plurality of columns of bristle bundles, where the rows aligned parallel to the longitudinal axis of the brush head portion, and the columns are aligned perpendicular to the longitudinal axis of the brush head portion. The bristles in each bundle in each row of bristle bundles are substantially equal in length, and the lengths of the bristles in each row of bristle bundles on each bristle head portion are progressively longer in each successive row of bristle bundles which is further away from the longitudinal axis of the brush head portion than an adjacent row of bristle bundles which is closer to the longitudinal axis of the brush head portion. The outer ends of the respective row of bristle bundles on each bristle head portion which is closest to the longitudinal axis of the brush head portion are spaced less than 0.100 inch from the outer ends of the respective opposed row of bristle bundles on the other bristle head portion.

17 Claims, 4 Drawing Sheets

ELECTRIC TOOTHBRUSH HAVING OPPOSED BRISTLE HEADS

FIELD OF THE INVENTION

This invention relates to electric toothbrushes, sometimes referred to as mechanical toothbrushes, and is more particularly directed to a portable hand-held, electrically powered, mechanical toothbrush. Specifically, a novel toothbrush head is disclosed.

BACKGROUND OF THE INVENTION

The use of manual toothbrushes has, of course, been know for many years. Indeed, the use of mechanical toothbrushes, typically those which are electrically driven, has been known for a number of years. The purpose, in any event, is to clean the teeth, usually with a toothbrush which comprises a plurality of bristles that are used in conjunction with a dentifrice. Very often, the dentifrice is mildly abrasive.

The dental profession has propounded, for many years, a technique known as the "Bass Technique" which, if properly performed, is said to achieve superior results in terms of cleaning one's teeth using a manual toothbrush. Essentially, the Bass Technique requires the user to position a manual toothbrush over a zone of the teeth, and then to use very short stokes so as to more or less vibrate the brush at that zone where the brush has been located. This short-stroke brushing should continue for a period of time—typically, twenty strokes to forty strokes—so as to remove any foreign material from that zone. The brush is then repositioned and typically another twenty to forty short strokes are performed. Because each zone is very small, the Bass Technique can be very time consuming. Moreover, since it is a requirement that the strokes be very short which, in turn, requires excellent muscle control, exercising the Bass Technique can be very tiring.

The theory is that, at the end of any given stroke, the bristles will flex so as to become oriented in such a manner that the ends of the bristles point generally away from the direction of the travel of the bristles across the teeth. However, at the beginning of the next stroke, in the opposite direction, the still-flexed bristles will then be pointed in the direction of the stroke and this may cause the bristle to chisel the foreign material away from the teeth for a moment before the bristle again begins to flex so as to sweep across the surface of the tooth in the zone where it is located.

Even if a person were able to maintain a vigorous pace of three strokes per second, the typical performance of a Bass Technique cleansing of the teeth would take more than four minutes. Typically, most people will quit brushing their teeth after about one minute. Therefore, while excellent in theory, the Bass Technique is impractical.

A purpose of the present invention is to provide an electromechanical toothbrush—that is, an electrically driven, mechanical toothbrush, most typically referred to as an electric toothbrush—which will permit the user to perform a tooth cleaning procedure which essentially emulates the Bass Technique. In other words, by using the toothbrush of the present invention, the user will be able to locate the toothbrush at a given zone for a short period of time, while executing a plurality of very short strokes quite rapidly, and then move on to the next zone while having achieved efficient cleaning of the teeth.

Apart from the removal of leftover food particles and the like, a particular purpose for cleaning the teeth is to remove plaque build-up from the teeth. Typically, when using a manual toothbrush, plaque build-up is removed much more easily from the buccal surfaces of the teeth than from the lingual surfaces of the teeth, with relatively good foreign material removal from the occlusal surfaces of the teeth also being achieved.

One development that has occurred in respect of manual toothbrushes is the provision of twin-headed brushes, whereby the lingual and buccal surfaces of the tooth can be scrubbed using the bristles of the brush at the same time, with the same stroking action of the brush.

As to electric toothbrushes, most electric toothbrushes provide groups of bristles which are located in concentric circles, where the brush head thus provided is rotated or, more usually, it is reciprocally rotated.

DESCRIPTION OF THE PRIOR ART

Several typical prior art toothbrushes are now described. Among them are several manual toothbrushes which comprise dual, opposed bristle heads. They include PORPER U.S. Design Pat. No. D259,977, issued Jul. 28, 1981, which reveals an early design for a toothbrush having opposed bristle heads.

Another manual toothbrush which is adapted for cleaning multiple sides of the teeth at the same time is shown in WAGNER U.S. Pat. No. 5,327,607, issued Jul. 12, 1994.

The toothbrush disclosed in that patent includes further bristles which extend from the spine of the toothbrush so as to contact the occlusal surfaces of the teeth at the same as the buccal and lingual surfaces of the teeth are being contacted while the toothbrush is in use.

A typical prior art electric toothbrush is disclosed in AMAKASU U.S. Pat. No. 5,359,747, issued Nov. 1, 1994. Here, a brush member of the toothbrush is given reciprocal motion in the axial direction while, at the same time, the brush member itself is given a rotary motion. The rotary brush member is rotatably mounted on the end of an attachment connected to a drive shaft, and the reciprocating motion in the axial direction thereof is converted into a rotary motion and transmitted to the rotary brush member by a second transmission mechanism.

Another typical prior art electric toothbrush is disclosed in BAUMAN U.S. Pat. No. 5,353,460, issued Oct. 11, 1994. Here, there is a pair of brush elements with driving mechanism which drives one of the brush elements in oscillation, with linkage between the brush elements so that the second brush element is also driven in oscillation. The two brush elements are preferably oscillated in opposite directions. However, the two brush elements can only contact any one surface of the teeth at a time.

A mechanical toothbrush which is said to effectively replicate the Bass Technique is STANSBURY U.S. Pat. No. 5,259,083, issued Nov. 9, 1993. This power driven mechanical toothbrush comprises a plurality of tuft blocks which are mounted on a cam shaft. The tuft blocks are received in sliding relation in a toothbrush head member, and each tuft block slides linearly in a direction parallel to the longitudinal tuft axis as it is guided by guide rails within the head member between a retracted position and an extended position. The tuft blocks are each driven by the rotatable cam. In use, the tuft bristles are brought into contact with the teeth by the user, before the respective tuft block reaches its extended position, so as to thereby flex the bristles and to cause a lateral motion of the distal end of the bristles along the surface of the teeth. This whipping action of the ends of the bristles causes a wiping action across the surface of the teeth while, at the same time, causing a chiselling action by the ends of the bristles against the teeth, so as to thereby remove foreign material away from the teeth in the region where the bristle chiselling action occurs.

Finally, DAUB U.S. Pat. No. 5,027,463, issued Jul. 2, 1991, teaches a toothbrush which may be used for simultaneously brushing and cleaning the occlusal, lingual, and buccal surfaces of the upper and lower teeth of the user. Here, a bristle support member is provided which anchors bristles which extend from the opposite surfaces thereof. The bristles are arranged so that the central rows of bristles are straight while the intermediate and outer rows of bristles on each of the opposed surfaces of the bristle support member are curved. The straight bristles will engage the occlusal surfaces of the teeth, while the intermediate and outer rows will engage the lingual and buccal surfaces of the teeth.

SUMMARY OF THE INVENTION

In accordance with one aspect of the present invention, there is provided an electric toothbrush which comprises a power handle portion and a brush head portion. The power handle portion has a longitudinal axis, and is adapted to provide a housing for an electric motor and for a driving mechanism located at a first end of the power handle portion. The driving mechanism is powered by the electric motor, and includes a drive shaft having a longitudinal axis, the drive shaft being adapted for frictional coupling to a drive pin mounted on the brush head portion.

The drive shaft is driven by the electric motor so as to effect a linear reciprocating motion in a direction along its longitudinal axis.

The brush head portion has a longitudinal axis, and is removably attachable at a first end thereof to the first end of the power handle portion. The brush head portion comprises a drive pin located at a first end thereof for frictional coupling in force transmitting relationship with the drive shaft. The drive pin is aligned along the longitudinal axis of the brush head portion.

The brush head portion further comprises a pair of opposed bristle head portion arranged so as to present two groups of opposed bundles of bristles disposed substantially perpendicularly each to the other. Each of the groups of bundles of bristles on each respective bristle head portion comprises a plurality of row and a plurality of columns of bristle bundles, where the row of bristle bundles are aligned parallel to the longitudinal axis of the brush head, and the columns of bristles are aligned perpendicular the longitudinal axis of the brush head.

The bristles in each bundle in each row of bristle bundles on each bristle head portion are substantially equal in length. The length of the bristles in the respective row of bristle bundles on each bristle head portion which is closest to the longitudinal axis of the brush head portion is shorter than the length of the bristles in the respective row of bristle bundles on each bristle head portion which is furthest away from the longitudinal axis of the brush head portion. Moreover, the lengths of the bristles in each respective row of bristle bundles on each bristle head portion are progressively longer in each row of bristle bundles which is further away from the longitudinal axis of the brush head portion than an adjacent row of bristle bundles which is closer to the longitudinal axis of the brush head portion.

The outer ends of the respective row of bristle bundles which is closest to the longitudinal axis of the brush head portion, on each of the bristle head portions, are spaced less than 0.100 inch from the outer ends of the respective opposed row of bristle bundles on the other bristle head portion.

A reciprocating linear motion is imparted to the brush head portion, and thus to each of the opposed bristle head portions, and the reciprocating linear motion of the brush head portion is in a direction parallel to its longitudinal axis.

In keeping with a particular feature of the present invention, as described in greater detail hereafter, the brush head portion comprises two matched halves, and the drive pin. Each of the two matched halves comprises a respective one of the bristle head portions and a respective half of an intermediate arm portion of the brush head portion. Each respective matched half is formed with a socket portion near the first end thereof in the respective half of the intermediate arm portion. The socket portion is disposed near the longitudinal axis of the brush head portion. The drive pin is conformed with a boss portion at an end thereof which is remote from the end which engages the drive shaft, and the boss portion and the respective socket portions of the matched halves are such that, when the matched halves are assembled one to the other, the boss portion of the drive pin is captured and secured by the respective socket portions of the matched halves. Thus, driving power for the linear reciprocating motion of the brush head is transmitted to the drive pin from the drive shaft, and is directly transmitted to the brush head portion due to the fitment of the boss portion of the drive pin in the respective socket portions of the matched halves of the brush head.

A further aspect of the present invention is to provide such an electric toothbrush as is described above, where the brush head portion further comprises a collar portion at the first end thereof, which collar portion is adapted to be removably attachable to the first end of the power handle portion. The opposed bristle head portions of the brush head portion are disposed at the end of an intermediate arm portion thereof, which end is opposed to the first end of the brush head portion. The intermediate arm portion is accommodated within the collar portion in such a manner that it is free for linear reciprocating motion relative to the collar portion, along the longitudinal axis of the brush head.

A purpose of the present invention is to provide such an electric toothbrush as described above, which can be used to effectively emulate the Bass Technique and, thereby, to achieve better tooth cleaning results.

Finally, a purpose of the present invention is to bring an electric toothbrush to the market which can be used for very effective cleaning of the teeth, but which can be brought to the market at relatively low cost compared with many of the prior art electric toothbrushes, due to the relatively uncomplicated structure of the electric toothbrush hereof.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

In a paper published in the *Journal of Clinical Paediatric Dentistry*, Vol. 19, No. 1, Fall 1994, ALMAJED describes the superior results obtained by thirty patients ranging in age between 6.6 and 18 years of age, using a double-headed toothbrush, compared with an ordinary manual toothbrush, with and without dentifrice. The double-headed toothbrush is identified with the trade mark TWINBRUSH, provided by Prevention Health Products, Inc. of Somers, New York, U.S.A., and being that which is identified in Porper U.S. Design Pat. No. D259,977, noted above. The results of the tests were such that, even with manual manipulation of the double-headed toothbrush, it was significantly more effective in removing plaque than the single-headed toothbrush. The technique used by the patients is identified as being a modified Bass Technique. The results obtained were statistically significant.

As noted above, a feature of the present invention is essentially to provide a double-headed brush head which effectively replicates that which is shown in the Porper design patent, but with a modified arrangement of rows and columns of bunches of bristles in a preferred embodiment and, in any event, arranged in such a manner so as to be mechanically driven as the brush head portion of an electric toothbrush.

Figure 1:
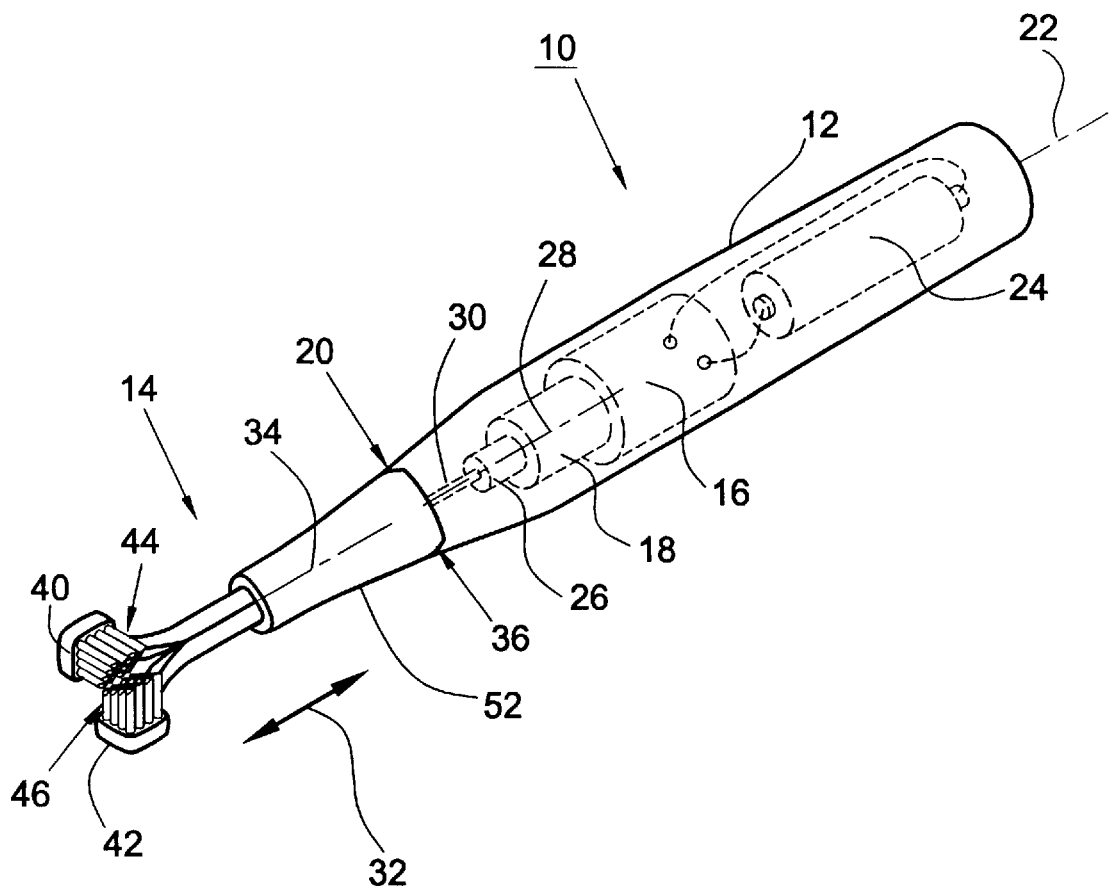
FIG. 1 is a simplified perspective view of a toothbrush in keeping with the present invention, showing several typical power components thereof in ghost fashion.

A typical configuration of electric toothbrush, in keeping with the present invention, is now described with reference first to FIG. 1. The electric toothbrush 10 comprises a power handle portion 12 and a brush head portion 14. Typically, there is included in the power handle portion 12 an electric motor 16 and a driving mechanism 18, which is driven by the electric motor 16. The precise details of the electric motor and the driving mechanism are outside the realm of the present invention. However, it will be noted that the driving mechanism is located at or near a first end 20 of the power handle portion 12. It will also be noted that the power handle portion 12 has a longitudinal axis, which is indicated at 22.

Typically, the electric motor 16 is a direct current motor. Even more typically, the direct current motor is powered by a battery 24, which is usually a rechargeable battery. However, it is evident that the electric motor 16 might also be an alternating current motor; or even that the battery 24 might be replaced by a power supply circuit providing low voltage direct current power to the electric motor, whereby the electric toothbrush 10 may be plugged directly into a suitable receptacle. All of those matters are, again, outside the scope of the present invention.

In keeping with the present invention, the driving mechanism 18 includes a drive shaft 26, which has its own longitudinal axis 28. The drive shaft 26 is arranged, particularly in a manner described in greater detail hereafter, for frictional coupling to a drive pin 30 which is mounted on and extends from the brush head portion 14 of the electric toothbrush of the present invention.

The drive shaft 26 is driven by the electric motor 16 in such a manner as to effect a linear reciprocating motion in a direction along its longitudinal axis 28. That linear reciprocating motion will, as described hereafter, result in a concomitant linear reciprocating motion of the brush head portion 14 in a manner as shown by double-headed arrow 32.

The brush portion 14 also has a longitudinal axis shown at 34. The brush head portion 14 is removably attachable at a first end 36 from the first end 20 of the power handle portion 12. When removed, the brush head portion 14 typically may have an appearance such as that shown in FIG. 3.

Figure 2:
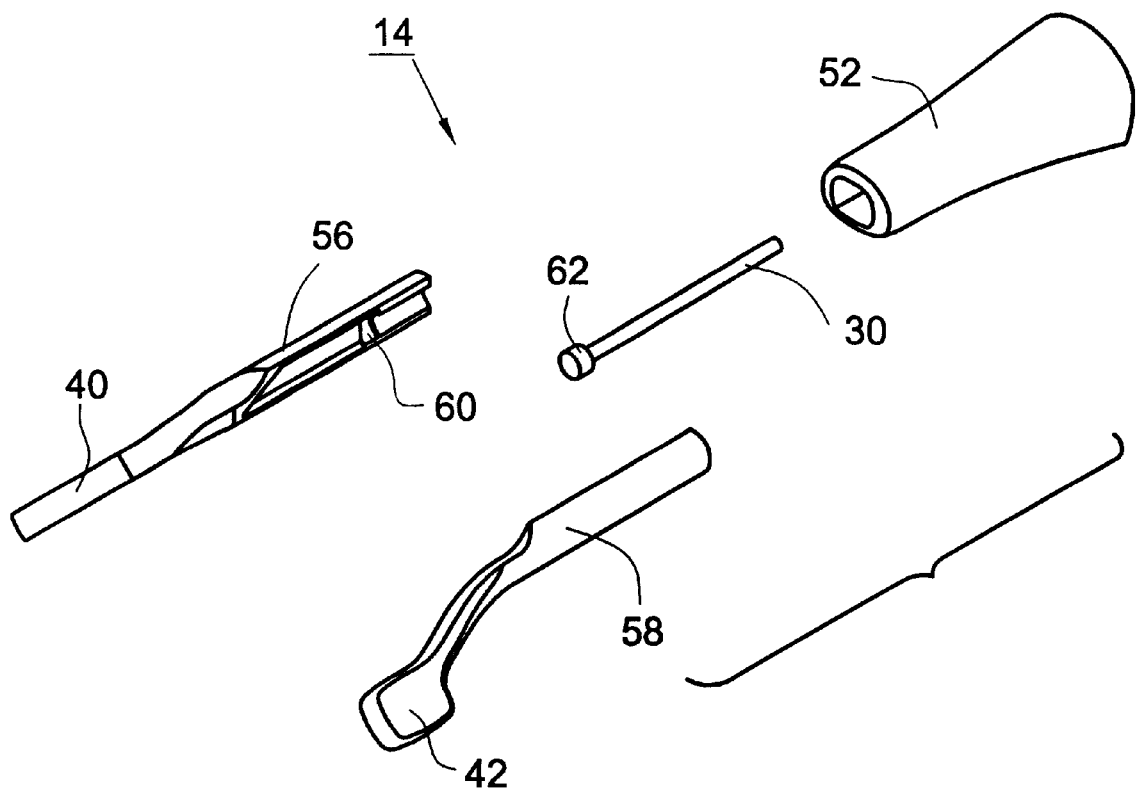
FIG. 2 is an exploded view showing assembly of the brush head portion of the present invention.
Figure 3:
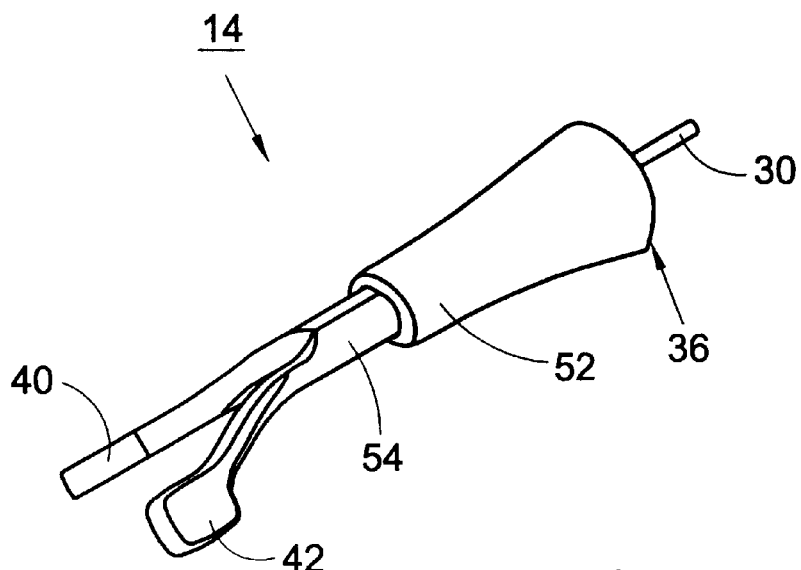
FIG. 3 shows the brush head portion with the components of FIG. 2 being in assembled condition.

Turning now to FIGS. 2 and 3, the following discussion is particularly directed to the brush head portion 14, and a typical manner in which it is assembled. Further advantages of the assembly of the brush head portion 14, in keeping with a preferred embodiment of the present invention, will be described hereafter. As noted, the brush head portion 14 includes a drive pin 30 which is located at its first end 36. The drive pin 30 is arranged for frictional coupling in force transmitting relationship with the drive shaft 26. Typically, the drive shaft 26 is conformed with a socket (not shown) at or near the first end 20 of the power handle portion 12, so as to receive the drive pin 30 in frictional driving relationship therewith. Accordingly, in that arrangement, and in keeping with a preferred embodiment of the present invention, the longitudinal axis 28 of the drive shaft 26, and the longitudinal axis 34 of the brush head portion 14, are co-linear. Obviously, of course, the drive pin 30 is aligned along the longitudinal axis 28 of the drive shaft 26.

The brush head portion 14 comprises a pair of opposed bristle head portions 40 and 42. The bristle head portions 40 and 42 are arranged so as to present two groups of opposed bundles of bristles, indicated at 44 and 46; and the groups of opposed bundles of bristles 44 and 46 are disposed substantially perpendicularly each to the other as shown particularly in FIG. 4.

Each of the groups of bundles of bristles on each of the respective bristle head portions 40 and 42 comprises a plurality of rows and a plurality of columns of bristle bundles. For example, FIG. 7B shows four rows and four columns of bristle bundles, whereas FIG. 8B shows three rows and four columns of bristle bundles. It is obvious, therefore, that the rows of bristle bundles are aligned parallel to the longitudinal axis 34 of the brush head portion 14, and the columns of bristle bundles are aligned perpendicular to the longitudinal axis 34 of the brush head portion 14.

Figure 4:
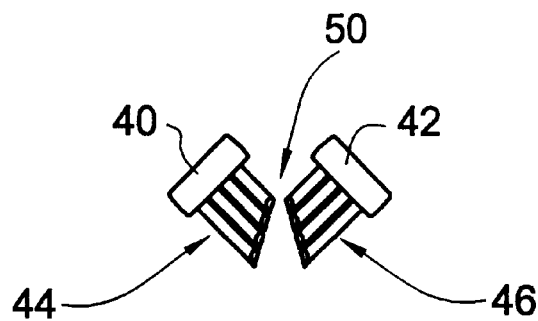
FIGS. 4, 5, and 6 are end views of the brush head portion of the toothbrush, and of the brush head portion of the toothbrush being in contact with a typical tooth at the rear of the mouth, and in contact with a typical tooth at the front of the mouth, respectively.
Figure 7A:
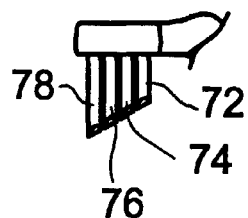
FIGS. 7A, 7B, 7C, and 8A, 8B, and 8C are end, plan, and elevational views, respectively, of two typical configurations of the bristle head portion of a toothbrush in keeping with the present invention.
Figure 7B:
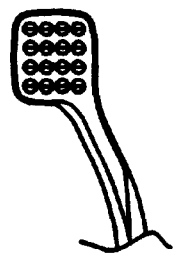
Figure 7C:
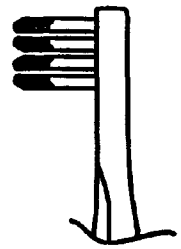
Figure 8A:
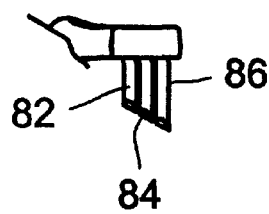
Figure 8B:
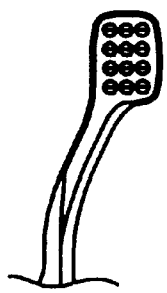
Figure 8C:
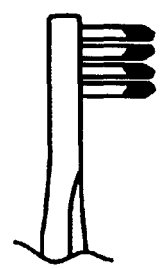

Moreover, it is seen in each of FIGS. 4, 7A, and 8A, in particular, that the bristles in each bundle in each row of bristle bundles on each bristle head portion 40 or 42 are substantially equal in length. Still further, it is evident from an inspection of the Figures of drawings, particularly FIGS. 4, 7A, and 8A, that the length of the bristles in the respective row of bristle bundles on each of the bristle head portions 40 and 42 which is closest to the longitudinal axis of the brush head portion 14, is shorter than the length of the bristles in the respective row of bristles bundles on each bristle head portion 40 and 42 which is furthest away from the longitudinal axis of the brush head portion 14. Thus, for example, the length of the bristle bundles 72 shown in FIG. 7A is shorter than the length of each of the bristle bundles 78. The same conditions apply with respect to bristle bundles 82 and 86 shown in FIG. 8A.

Still further, the lengths of the bristles in each of the intervening rows of bristle bundles on each bristle head portion are progressively longer in each row of bristle bundles which is further away from the longitudinal axis of the brush head portion than an adjacent row of bristle bundles which is closer to the longitudinal axis of the brush head portion. Thus, the length of the bristle bundles 72 is shorter than the length of the bristle bundles 74 which, in turn, is shorter than the length of the bristle bundles 76, which is shorter again than the length of the bristle bundles 78, all as seen in FIG. 7A. Likewise, the length of the bristle bundles 84, shown in FIG. 8A, is intermediate to the lengths of the bristle bundles 82 and 86.

Typically, the longest bristles 78 or 86 will range in length from about 0.375 inch up to about 0.45 inch, although those dimensions are exemplary only. Also, as typical examples, the length of a bristle head portion having four columns of bristle bundles may be slightly less than one-half inch; whereas the width of a bristle head portion having four row of bristle bundles, as shown in FIG. 7B, might be in the range of 0.45 inch, while the width of a bristle head portion having only three rows of bristle bundles, such as that shown in FIG. 8B, may be in the range of 0.365 inch.

As will be described in greater detail hereafter, the inner rows of bristle bundles—that is, the rows of bristle bundles which are closest to the longitudinal axis of the brush head portion 14—are arranged so that the outer ends or tips of the bristle bundles are nearly touching each other, as can be seen particularly in FIG. 4. The gap 50 which is between the outer ends of the respective rows of bristle bundles which are closest to the longitudinal axis of the brush head portion, and each of the bristle head portions 40 and 42, may typically be less than 0.100 inch, but may be more or less than that dimension.

Thus, it can be seen that, when the electric toothbrush 10 is turned on by a switch (not shown) and the electric motor 16 drives the driving mechanism 18 and the drive shaft 26 to impart a reciprocating linear motion from the drive shaft 26 through the drive pin 30 to the brush head portion 14, and thus to each of the opposed bristle head portions 40 and 42, the reciprocating linear motion is as indicated by the double-headed arrow 32, and is effected in a direction parallel to the longitudinal axis 34 of the brush head portion 14.

Typically, all of the longitudinal axes 34, 28, and 22, are co-linear one with another, whereby the longitudinal axis 22 of the handle portion 12 is co-linear with the longitudinal axis 28 of the drive shaft 26 and driving mechanism 18. It has been previously stated that, in any event, the longitudinal axes 28 of the drive shaft 26, and 34 of the brush head portion 14, are co-linear so as to effect the transfer of driving power from the drive shaft 26 through the drive pin 30 to the bristle head portions 40 and 42.

Referring particularly to FIGS. 2 and 3, the brush head portion 14 is seen to further comprise a collar portion 52. The collar portion 52 includes the first end 36 of the brush head portion 14, and is adapted to be removably attachable to the first end 20 of the power handle portion 12. Typically, that attachment is a slide or snap fitment, and is such as to protect the area where the drive pin 30 is frictionally secured to the drive shaft 26. However, it will be evident that the bristle head portion 42 and an intermediate arm portion 54 of the brush head portion 14 are freely moveable along the longitudinal axis 34 of the brush head portion 14, within the collar portion 52. The opposed bristle head portions 40 and 42 are disposed at the end of the intermediate arm portion 54 which is opposite the first end 36 of the brush head portion 14. As noted, the intermediate arm portion 54 is accommodated within the collar portion 52 in such a manner as to be free for linear reciprocating motion relative to the collar portion 52, along the longitudinal axis 34 of the brush head portion 14.

Typically, the length of each stroke of the reciprocating linear motion of each of the opposed bristle head portions 40 and 42 is in the range of from 0.075 inch up to 0.250 inch. A typical stroke length is one-eighth of an inch; or, having regard to ordinary tolerances, one-eighth of an inch may be considered to be in the range of from 0.115 inch to 0.135 inch.

Still having regard to the stroke characteristics undergone by the opposed bristle head portions 40 and 42, the rate at which the reciprocating linear motion of each of those opposed bristle head portions 40 and 42 is effected is typically in the range of from 500 strokes per minute up to 2,000 strokes per minute. Thus, it will be seen that effective emulation of the Bass Technique may be attained.

Referring especially to FIG. 2, the assembly of the brush head portion 14 is described.

It will be seen that the brush head portion 14 typically comprises two matched halves 56 and 58, together with the drive pin 30. Each of the matched halves 56 and 58 is, essentially, a mirror image of the other; and each comprises a respective one of the bristle head portions 40 and 42 and a respective half of the intermediate arm portion 54.

In each of the respective matched halves 56 and 58, there is formed a socket portion 60 which is located near the first end 36, in each respective half of the intermediate arm portion 54. Only the socket 60 in the matched half 56 is visible in FIG. 2. Each socket portion 60 is disposed near the longitudinal axis 34 of the brush head portion 14.

Moreover, the drive pin 30 is configured with a boss portion 62 at the end thereof which is remote from the end which engages the drive shaft 26. The boss portion 62 and the respective socket portions 60 of the matched halves 56 and 58 are such that, when the matched halves are assembled one to the other, the boss portion 62 of the drive pin 30 is captured and secured by the respective socket portions 60 of the matched halves 56 and 58. Thus, driving power which is delivered from the drive shaft 26 to the drive pin 30, so as to provide for the linear reciprocating motion of the bristle head portions 40 and 42, is transmitted to the drive pin 30 from the drive shaft 26, and the driving power is directly transmitted through the boss portion 62 to the socket portion 60 and thence directly to the brush head portion 14 because of the fitment of the boss portion 62 of the drive pin 30 in the respective socket portions 60 of the matched halves 56 and 58.

Generally, the matched halves 56 and 58 of the brush head portion are assembled to each other by being sonically welded to each other. However, they may also be easily glued to each other. This is especially true when, as is typical, the material from which the two matched halves 56 and 58 of the brush head portion have been manufactured is ABS (acrylonitrile butadiene styrene). This factor becomes important when it is considered that a typical material from which the drive pin 30 is manufactured is nylon. The drive shaft 26 is typically stainless steel, and a nylon drive pin provides both strength and durability for the frictional connection to the stainless steel drive shaft. However, nylon is not easily glued or sonically welded to ABS; but, by capturing the boss 62 in the socket 60 and solidly securing the matched halves 56 and 58 together by sonically welding or gluing, secure engagement of the drive pin 30 is assured.

Still further, sufficiently close manufacturing tolerances can be assured so that there is substantially zero longitudinal clearance, or difference in the longitudinal length of the boss 62 and the socket 60, so that there is no slop or loose driving arrangement between the drive pin 30 and the intermediate arm portion 54 of the brush head portion 14.

While referring to FIG. 2, it is evident that the manufacture of a double-headed toothbrush may be very easily arranged. Specifically, the bristle head portions 40 and 42 may be populated with the bristle bundles, the ends of the bristle bundles trimmed and rounded, and whatever other manufacturing step is required for the bristles may be attended to, without any regard to the opposed bristle head. This is because the matching halves 56 and 58 are, obviously, separately molded. Previously, double-headed toothbrushes such as that shown in Porper Design Pat. No. D259,977, were molded flat, and the bristle head portions were populated with bristle bundles, trimmed and end-rounded, but with some difficulty due to the close proximity of the other bristle head. Thereafter, the respective bristle head portions were required to be bent or post-formed using heat and, thus, their alignment and spatial relationship with each other is less exact than can be accomplished by the present invention where the matched halves 56 and 58 are manufactured separately and merely require to be assembled to each other, as described above.

Figure 5:
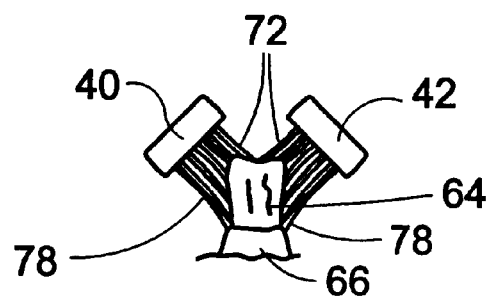
Figure 6:
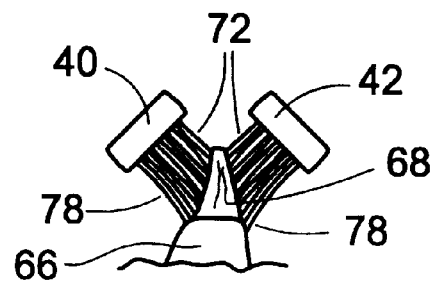

Finally, referring to FIGS. 5 and 6, the advantage of the present invention will become obvious. In FIG. 5, a typical molar 64 is shown together with its supporting gum structure 66. It is seen that the inner bristle bundles 72 on the respective bristle head portions 40 and 42 engage and will clean the occlusal surface of the tooth 64, whereas the remaining bristle bundles will engage and clean the buccal and lingual surfaces of the tooth 64. As described above, because the stroke length is very short, being in the range of 0.125 inch, and the stroke frequency is in the range of 500 strokes per minute to 2,000 strokes per minute, the ends of the bristle bundles will be bent and will be constantly changing directions. They will, therefore, probe around the occlusal, buccal, and lingual surfaces of the tooth, and the probe will be effected with limited sweeping action.

Indeed, it is believed that use of many typical prior art electric toothbrushes, particularly those which cause a sweeping motion either rotationally or longitudinally, particularly when combined with the use a typical abrasive dentifrice, actually causes thinning of the tooth enamel. Thus, the rapid but very short strokes of the toothbrush of the present invention are much less likely to cause enamel thinning or other damage to the teeth while, at the same time, providing a more efficient cleaning action due to the short stroke and the constantly changing direction of motion of the bristle ends.

The same conditions are noted in FIG. 6, where a typical front tooth 68 is shown, having its buccal and lingual surfaces cleaned, as well as its occlusal surface to the extent that such surface exists.

The user of the tooth brush in keeping with the present invention may wish to slightly rock the toothbrush about its longitudinal axis, but that is not necessary. Moreover, it is evident that there is no necessity for there to be any great amount of pressure applied by the user in pressing the bristles of the bristle head portions against the teeth. However, if more than sufficient pressure is applied, this may result in slowing down of the electric motor 16 and, thus, there may be no substantial change in the amount of torque available at the ends of the bristle bunches, even though the pressure between the bristles and the teeth may change.

There has been described an electric toothbrush which exhibits obvious advantages over prior art electric toothbrushes, and which particularly provides an apparatus which will effectively emulate the highly promoted but heretofore impossible to achieve Bass Technique for brushing the teeth. The precise materials of the bristles and their manufacture are well know to the industry, as is the provision of a suitable power handle portion having an appropriate electric motor and linear reciprocating motion drive shaft. However, their application to an electric toothbrush in keeping with the present invention falls within the scope of the accompanying claims.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantial" and/or "substantially" when used with an adjective or adverb is intended to enhance the scope of the particular characteristic; e.g., substantially equal is intended to mean equal, nearly equal and/or exhibiting characteristics associated with equality.

What is claimed is:

1. An electric toothbrush comprising a power handle portion and a brush head portion;

said power handle portion having a longitudinal axis, and being adapted to provide a housing for an electric motor and for a driving mechanism located at a first end of said power handle portion;

said driving mechanism being powered by said electric motor, and including a drive shaft having a longitudinal axis, and being adapted for frictional coupling to a drive pin mounted on said brush head portion;

said drive shaft being driven by said electric motor so as to effect a linear reciprocating motion in a direction along its longitudinal axis;

said brush head portion having a longitudinal axis, and being removably attachable at a first end thereof to said first end of said power handle portion;

said brush head portion comprising a drive pin located at said first end thereof for frictional coupling in force transmitting relationship with said drive shaft, said drive pin being aligned along said longitudinal axis of said drive shaft;

said brush head portion further comprising a pair of opposed bristle head portions arranged so as to present two groups of opposed bundles of bristles disposed substantially perpendicularly each to the other;

each of said groups of bundles of bristles on each respective bristle head portion comprising a plurality of rows and a plurality of columns of bristle bundles, where the rows of bristles bundles are aligned parallel to the longitudinal axis of said brush head portion, and the columns of bristle bundles are aligned perpendicular to the longitudinal axis of said brush head portion;

wherein the bristles in each bundle in each row of bristle bundles on each bristle head portion are substantially equal in length, where the length of the bristles in the respective row of bristle bundles on each bristle head portion which is closest to the longitudinal axis of said brush head portion is shorter than the length of the bristles in the respective row of bristle bundles on each bristle head portion which is furthest away from the longitudinal axis of said brush head portion, and wherein the lengths of the bristles in each respective row of bristle bundles on each bristle head portion are progressively longer in each row of bristle bundles which is further away from the longitudinal axis of said brush head portion than an adjacent row of bristle bundles which is closer to the longitudinal axis of said brush head portion;

whereby a reciprocating linear motion is imparted to said brush head portion and thus to each of said opposed bristle head portions, and said reciprocating linear motion is in a direction parallel to said longitudinal axis of said brush head portion.

2. The electric toothbrush of claim 1, wherein said drive shaft is configured with a socket at said first end of said power handle portion to receive said drive pin in frictional driving relationship therewith, whereby the longitudinal axis of said drive shaft and the longitudinal axis of said brush head portion are co-linear.

3. The electric toothbrush of claim 2, wherein the longitudinal axis of said handle portion and the longitudinal axis of said drive shaft are co-linear.

4. The electric toothbrush of claim 1, wherein said brush head portion further comprises a collar portion at the first end thereof, which is adapted to be removably attachable to the first end of said power handle portion, wherein said opposed bristle head portions are disposed at the end of an intermediate arm portion which is opposite said first end of said brush head portion, and wherein said intermediate arm portion is accommodated within said collar portion in such a manner as to be free for linear reciprocating motion relative to said collar portion, along said longitudinal axis of said brush head portion.

5. The electric toothbrush of claim 4, wherein said brush head portion comprises two matched halves and said drive pin;

wherein each of said two matched halves comprises a respective one of said bristle head portions and a respective half of said intermediate arm portion;

wherein each respective matched half is formed with a socket portion near said first end thereof in said respective half of said intermediate arm portion, said socket portion being disposed near the longitudinal axis of said brush head portion;

wherein said drive pin is configured with a boss portion at an end thereof remote from the end which engages said drive shaft, said boss portion and the respective socket portions of said matched halves being such that when said matched halves are assembled one to the other, said boss portion of said drive pin is captured and secured by said respective socket portions of said matched halves;

whereby driving power for said linear reciprocating motion which is transmitted to said drive pin from said drive shaft is directly transmitted to said brush head portion by the fitment of said boss portion of said drive pin in said respective socket portions of said matched halves.

6. The electric toothbrush of claim 5, wherein said matched halves of said brush head portion are assembled to each other by being glued to each other.

7. The electric toothbrush of claim 5, wherein said matched halves of said brush head portion are assembled to each other by being sonically welded to each other.

8. The electric toothbrush of claim 5, wherein the material from which each of said two matched halves has been manufactured is ABS, and the material form which said drive pin has been manufactured is nylon.

9. The electric toothbrush of claim 1, wherein said reciprocating linear motion of each of said opposed bristle head portions has a stroke length in the range of 0.075 inch to 0.250 inch.

10. The electric toothbrush of claim 1, wherein the stroke length is in the range of 0.115 inch to 0.135 inch.

11. The electric toothbrush of claim 1, wherein the rate at which said reciprocating linear motion of each of said opposed bristle head portions is effected is in the range of 500 strokes per minute to 2,000 strokes per minute.

12. The electric toothbrush of claim 1, wherein each of said bristle head portions of said brush head portion comprises four rows and four columns of bristle bundles.

13. The electric toothbrush of claim 1, wherein each of said bristle head portions of said brush head portion comprises three rows and four columns of bristle bundles.

14. The electric toothbrush of claim 1, wherein said electric motor is an alternating current motor.

15. The electric toothbrush of claim 1, wherein said electric motor is a direct current motor.

16. The electric toothbrush of claim 15, wherein said power handle portion further comprises a battery for said direct current motor.

17. The electric toothbrush of claim 16, wherein said battery is rechargeable.

* * * * *